United States Patent [19]

Hirashima et al.

[11] 4,374,250
[45] Feb. 15, 1983

[54] METHOD OF PRODUCING BENZIMIDAZOLONE

[75] Inventors: Tsuneaki Hirashima; Toshiyuki Miyata, both of Sakai, Japan

[73] Assignee: Osaka Municipal Government, Japan

[21] Appl. No.: 275,618

[22] Filed: Jun. 22, 1981

[30] Foreign Application Priority Data

Jun. 23, 1980 [JP] Japan .................................. 55-84701
Dec. 30, 1980 [JP] Japan ................................ 55-186986

[51] Int. Cl.³ .......................................... C07D 235/26
[52] U.S. Cl. ..................................... 548/305; 564/441
[58] Field of Search ......................................... 548/305

[56] References Cited

PUBLICATIONS

Falbe, J. (Editor), *New Syntheses with Carbon Monoxide*, Springer-Verlag, New York, 1980, pp. 291–292, 296–297, 302–307.

Sonoda, N., et al., *J. Am. Chem. Soc.*, 93, 6344 (1971).

Kondo, K., et al., *Angew. Chem. Int. Ed. Engl.*, 18, 692 (1979).

Kondo, K., et al., *Angew Chem. Int. Ed. Engl.*, 18, 691 (1979).

*Primary Examiner*—Richard A. Schwartz
*Attorney, Agent, or Firm*—Wenderoth, Lind & Ponack

[57] ABSTRACT

A method of producing benzimidazolone which comprises reacting a feed compound having the general formula

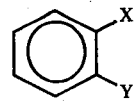

wherein X and Y independently represent an amino group or a nitro group, with carbon monoxide in solvent in the presence of selenium and a base, and in the presence of water when the feed compound has nitro groups.

14 Claims, No Drawings

METHOD OF PRODUCING BENZIMIDAZOLONE

The present invention relates to a method of producing benzimidazolone.

Benzimidazolone is widely used as intermediates for producing dyestuffs, pigments, medicines and other useful chemicals, and its use is now further expanding. However, the conventional methods of producing benzimidazolone have various disadvantages. For example, benzimidazolone has been for a long time produced by the reaction of o-phenylenediamine with phosgene or urea in solvent. These methods require severe reaction conditions, but provide benzimidazolone of poor purity in low yields. A further disadvantage of the methods is that o-phenylenediamine is not readily available, and hence expensive; it is produced usually by the nitration of chlorobenzene to o-nitrochlorobenzene, ammonolysis thereof to o-nitroaniline and then reduction thereof.

Therefore a method has been proposed using a feed material other than o-phenylenediamine in which o-dichlorobenzene is reacted with aqueous ammonia in the presence of carbonates or bicarbonates of alkali or alkaline earth metals and a catalyst composed of cuprous salts and metallic copper (Japanese Patent Disclosure No. 50-112367). However, it is difficult to apply this method to continuous process because of the use of metallic copper. Recovery and reuse of catalyst is also difficult since parts of catalyst components are converted into cupric salts, which must be separated from the recovered catalyst.

A further improved method therefore has been proposed to obviate the above disadvantages, in which o-dichlorobenzene is reacted with urea or ethylenecarbonate in the presence of either cuprous salts, cupric salts or a mixture of two salts in aqueous ammonia so as to make it easy to resue the catalyst (Japanese Patent Disclosure No. 54-24873). However, in the method it is necessary that the reaction be carried out at such a high temperature such as 220° C. under a high pressure such as 170–180 Kg/cm$^2$, and yet the method provides benzimidazolone only in low yield.

It is therefore an object of the present invention to provide a novel method of producing benzimidazolone which is simple in operation, mild in reaction conditions and is able to provide benzimidazolone of high purity in high yield.

It is another object of the invention to provide a method of producing benzimidazolone using a novel catalyst which is readily recovered and reused as is.

Other objects and features of the invention will become apparent from the following description and claims attached hereto.

According to the invention, there is provided a method of producing benzimidazolone which comprises reacting a feed material having the general formula

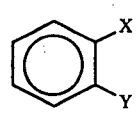

wherein X and Y independently represent an amino group or a nitro group, with carbon monoxide in solvent in the presence of selenium and an organic or inorganic base, and in the presence of water when the feed compound has nitro groups.

The feed compound used in the invention is preferably o-nitroaniline and o-phenylenediamine. o-Dinitrobenzene may be used as a feed compound if necessary. The feed compounds may have additional inactive substituents. The inactive substituent herein means any substituent which will not exert a harmful influence upon the reaction of the feed compound to benzimidazolone according to the reaction of the invention, and includes aliphatic, alicyclic and aromatic hydrocarbon residuals, heterocyclic residuals, alkoxy groups, aryloxy groups and halogens. For example, the inactive substituent may be methyl, ethyl, propyl, butyl, pentyl, hexyl, 2-ethylhexyl, cyclohexyl, phenyl, methoxy, ethoxy, propoxy, phenoxy, chlorine or bromine. According to the invention, for example, o-nitroaniline as well as o-phenylenediamine provide benzimidazolone in a single step reaction since the nitro group in the feed compound is simultaneously reduced to an amino group during the reaction in the presence of water as is explained later, and participates in the formation of imidazolone ring in cooperation with the amino at the ortho position.

In the invention is used selenium as a starting catalyst. This means that selenium is added to the reactants in solvent at the start of the reaction, but the selenium is converted into other forms during the course of reaction. Selenium used in the invention is preferably in the form of powder, and commercially available selenium powder is suitably used in the invention. Although the amount of selenium is not critical in the invention, and the more the amount of selenium used, the greater the reaction rate, selenium is used in the amount of 0.1 to 10 moles per mole of the feed compound so as to facilitate the recovery of selenium after the reaction. More usually 0.1 to 5 moles and preferably to 2 moles per mole of the feed compound are used.

In the reaction according to the invention, it is likely that selenium reacts with carbon monoxide in the presence of bases to provide selenium carbonyl (SeCO), which in turn reacts with water, if any in the reaction system, to provide selenium hydride (H$_2$Se). The selenium hydride will form a salt with a base and is dissolved in solvent. A nitro group when contained in the feed compound is reduced to an amino group by the selenium hydride, which in turn is oxidized to selenium, with the generation of water. The thus formed selenium however immediately reacts with carbon monoxide and then with water to generate selenium hydride. Accordingly, the reaction system of the invention is substantially homogeneous in almost all cases. On the other hand, selenium carbonyl inserts between the nitrogen and hydrogen atom of amino group of the feed compound to convert the amino into —NHCOSeH group, and the carbonyl carbon of the group attacks the amino group at the ortho position of the carbonyl group in an electrophilic manner, thereby forming benzimidazolone by ring closure, with the formation of selenium hydride.

Therefore, when the feed compound contains nitro group, water seems indispensable at least at the start of the reaction. Therefore, although not critical, water is added to the reactants usually in amounts of 1 to 100 moles per mole of selenium when the feed compound has nitro groups to be reduced to amino groups.

However, it should be understood that the present invention is not confined to any theory.

In the reaction of the invention, either inorganic or organic bases are used. As inorganic bases are used, for example, carbonates, bicarbonates, hydroxides, oxides and sulfides of alkali metals and alkaline earth metals. The sulfides include mono- and polysulfides. Preferable examples of inorganic bases are potassium carbonate, sodium carbonate, potassium hydroxide, sodium hydroxide, sodium sulfides and potassium sulfides. Nitrogen-containing organic bases are more preferred, and tertiary amines and N,N-dialkylamides are the most preferred. Examples are aliphatic tertiary amines such as triethylamine, tripropylamines, tributylamines, tri-2-ethylhexylamine, heterocyclic tertiary amines such as pyridine, alkylpyridine including picolines and lutidines, N-alkylpyrrolidines including N-methylpyrrolidines and N-alkylpyrrolidones including N-methylpyrrolidone. Further examples are N,N-dimethylformamide and N,N-dimethylacetamide.

The amounts of bases are not critical in the invention since bases may be used as solvents as described later, but usually 1 to 10 moles per mole of feed compound when a solvent other than the bases is used, preferably 2 to 5 moles per mole of feed compound.

The solvent used in the invention is either water or organic solvents which may contain water. The organic solvent used should give no harmful influences upon the reaction and should not be reduced in the reaction. Accordingly, preferable solvents used are ethers, amines, amides and hydrocarbons. The most preferred solvents are ethers such as diethylether, dipropylether, tetrahydrofuran and dioxane, tertiary amines such as triethylamine, pyridine and N-methylpyrrolidone, and N,N-dialkylamides such as N,N-dimethylformamide and N,N-dimethylacetamide. As will be apparent, the bases which are previously mentioned may be used as solvent. Hydrocarbons such as benzene and hexane may also be used as solvent if desired alone or in combination with other organic polar solvents such as aforesaid tertiary amines and ethers.

Water alone may be used as solvent, but since the reaction rate is relatively small in water as solvent, it is desired to use water together with other polar organic solvents such as aforesaid ethers and tertiary amines.

The reaction of the invention is carried out in an atmosphere of carbon monoxide, of which pressure is usually in the range of 1 to 100 $Kg/cm^2$, preferably 2 to 50 $Kg/cm^2$. Too a high pressure is preferably avoided so that undesired side reactions may not occur. The temperature of reaction is not critical, but usually in the range of room temperature to 200° C., preferably 50° to 100° C. The reaction will complete usually within ten hours, and in many cases four to five hours are sufficient for the reaction of the invention.

As previously mentioned, the reaction system of the invention is substantially homogeneous, and as a result selenium is readily recovered according to the invention. After the reaction air is introduced into the reaction mixture to decompose selenium compounds dissolved in the reaction mixture, thereby to precipitate black metallic selenium via red amorphous selenium. The selenium is filtered off from the reaction mixture, washed, and the thus recovered selenium can be reused as the catalyst as it is in the invention. The filtrate combined with the washings are distilled preferably under reduced pressure to leave benzimidazolone of high purity in high yields. The benzimidazolone thus obtained is so high in purity that further purification is not required for almost all purposes. When necessary, however, the product may be, for example, recrystalized from water.

The invention improves a prior method of producing benzimidazolone from o-phenylenediamine in purity and yield to a great extent, but a more important feature of the invention resides in a single step formation of benzimidazolone of high purity in high yield from o-nitroaniline, which is a feed material for o-phenylenediamine in the prior method. Furthermore, according to the invention, the reaction conditions are mild but also selenium is readily recovered and can be reused.

The invention will be understood more readily with reference to the following examples; however, these examples are intended to illustrate the invention and are not to be construed to limit the scope of the invention.

EXAMPLE 1 o-Nitroaniline 0.69 g (5 m moles), metallic selenium powder 0.20 g (2.5 m moles), water 0.66 g (37 m moles), triethylamine 5 ml (36 m moles) and tetrahydrofuran 20 ml were placed in a 100-ml capacity autoclave in a nitrogen atmosphere. The atmosphere in the autoclave was replaced by carbon monoxide of 5 $Kg/cm^2$. The contents were then heated to a temperature of 80° C. and held at the temperature with stirring for 3 hours, then cooled to room temperature, and carbon monoxide was removed from the autoclave by introducing air thereinto.

The reaction mixture was taken out of the autoclave, stirred in air for 2 hours to liberate metallic selenium as precipitates. The selenium was separated by filtration, washed with methanol. The filtrate combined with the washings were distilled off under reduced pressure to leave benzimidazolone 0.63 g (94.4% yield) as silver-white crystal. The thus obtained benzimidazolone has been found to have 97.6% purity upon high performance liquid chromatography.

EXAMPLES 2-4

Benzimidazolone was prepared from o-nitroaniline in a similar manner as above, and the results were shown in Table 1.

TABLE 1

| EXAMPLES | 2 | 3 | 4 |
|---|---|---|---|
| o-Nitroaniline (m moles) | 5.0 | 5.0 | 5.0 |
| Selenium (m moles) | 5.0 | 5.0 | 2.5 |
| Bases | TEA[1] | TEA | DMF[2] |
|  | 37 m mol | 37 m mol | 20 ml |
| Water (ml) | 0.66 | 40 | 0.66 |
| Solvents (ml) | THF[3] | — | — |
|  | 20 |  |  |
| CO-Pressure ($Kg/cm^2$) | 5 | 10 | 5 |
| Reaction temperatures (°C.) | 80 | 80 | 80 |
| Reaction times (hr) | 3 | 4 | 3 |
| Yields of benzimidazolone (%) | 99.0 | 67.3 | 75.0 |

[1]TEA = triethylamine
[2]DMF = dimethylformamide
[3]THF = tetrahydrofuran

EXAMPLE 5 o-Phenylenediamine 1.35 g (12.5 m moles), selenium powder 0.99 g (12.5 m moles), water 1.6 ml (89 m moles), triethylamine 5 g (50 m moles) and tetrahydrofuran 100 ml were placed in a 200-ml capacity autoclave, and the atmosphere therein was replaced by carbon monoxide of 20 $Kg/cm^2$. The contents in the autoclave were heated to 80° C. and held at the temperature for 3 hours with stirring. Thereafter the reaction mixture was cooled to room temperature, and carbon monoxide was removed from the autoclave. The reaction mixture was taken out of the autoclave and worked up in the same manner as in EXAMPLE 1 to provide benzimidazolone 1.66 g (99.0% yield) of 95.6% purity.

EXAMPLES 6-10

Benzimidazolone was prepared from o-phenylenediamine in a similar manner as in EXAMPLE 5, and the results were shown in Table 2.

EXAMPLE 11 o-Nitro-p-methylaniline 1.9 g (12.5 m moles), selenium powder 1.98 g (25 m moles), water 1.6 ml (89 m moles), triethylamine 5.0 g (50 m moles) and tetrahydrofuran 100 ml were placed in an autoclave, and kept at a temperature of 80° C. for 3 hours with stirring under carbon monoxide atmosphere of 20 Kg/cm$^2$. The reaction mixture was worked up in the same manner as in EXAMPLE 1, thereby providing 5-methylbenzimidazolone in 78.0% yield.

EXAMPLE 12 o-Dinitrobenzene 0.84 g (5.0 m moles), selenium 0.40 g (5.0 m moles), water 1.9 ml (35 m moles), triethylamine 4.0 g (40 m moles) and tetrahydrofuran 20 ml were placed in a 100-ml capacity autoclave, and stirred at a temperature of 80° C. for four hours under carbon monoxide atmosphere of 10 Kg/cm$^2$.

TABLE 2

| EXAMPLES | 6 | 7 | 8 | 9 | 10 |
|---|---|---|---|---|---|
| o-Phenylenediamine (m moles) | 12.5 | 12.5 | 12.5 | 12.5 | 12.5 |
| Selenium (m moles) | 6.3 | 12.5 | 12.5 | 12.5 | 12.5 |
| Bases | TEA 50 m mol | TEA 50 m mol | TEA 40 m mol | Py$^{(1)}$ 100 ml | TEA 50 m mol |
| Water (ml) | 1.6 | — | — | 1.6 | 100 |
| Solvent (ml) | THF 100 | THF 100 | THF 100 | — | — |
| CO-Pressure (Kg/cm$^2$) | 20 | 20 | 10 | 20 | 20 |
| Reaction temperatures (°C.) | 80 | 80 | 30 | 80 | 80 |
| Reaction times (hr) | 3 | 3 | 10 | 3 | 3 |
| Yields of benzimidazolone (%) | 88.0 | 97.3 | 89.0 | 72.3 | 67.5 |

$^{(1)}$Py = pyridine

The reaction mixture was worked up in the same manner as in EXAMPLE 1, and benzimidazolone 0.22 g (31% yield) was obtained.

What is claimed is:

1. A method of producing benzimidazolone which comprises reacting a reactant selected from the group consisting of o-nitroaniline or o-dinitrobenzene with carbon monoxide in a solvent in the presence of selenium, a base selected from the group consisting of tertiary amines, amides and inorganic bases selected from the group consisting of hydroxides, oxides, carbonates, bicarbonates and sulfides of alkali metals and alkaline earth metals, and water, said reactant containing no additional substituents or containing substituents which are substantially inert in said reaction.

2. The method as claimed in claim 1 wherein selenium is used in amounts of 0.1 to 10 moles per mole of reactant.

3. The method as claimed in claim 1 wherein the pressure of carbon monoxide is 1 to 100 Kg/cm$^2$.

4. The method as claimed in claim 1 wherein the organic base is a tertiary amine.

5. The method as claimed in claim 4 wherein the tertiary amine is a trialkylamine, pyridine, an alkylpyridine, an N-alkylpyrrolidone or an N-alkylpyrrolidine.

6. The method as claimed in claim 5 wherein the trialkylamine is triethylamine.

7. The method as claimed in claim 1 wherein the organic base is an N,N-dialkylamide.

8. The method as claimed in claim 7 wherein the N,N-dialkyl amide is N,N-dimethylformamide or N,N-dimethylacetamide.

9. The method as claimed in claim 1 wherein the inorganic base is an hydroxide, oxide, carbonate, bicarbonate or sulfide of an alkali metal or an alkaline earth metal.

10. The method as claimed in claim 9 wherein the alkali metal is potassium or sodium.

11. The method as claimed in claim 9 wherein the hydroxide is potassium hydroxide or sodium hydroxide.

12. The method as claimed in claim 1 wherein the reactant is o-nitroaniline and the final product is benzimidazolone.

13. The method as claimed in claim 1 wherein the reactant is o-dinitrobenzene and the compound II is benzimidazolone.

14. The method as claimed in claim 1 wherein the reactant is o-nitro-p-methylaniline and the final product is 5-methylbenzimidazolone.

* * * * *